(12) United States Patent
Hirano et al.

(10) Patent No.: US 7,214,494 B2
(45) Date of Patent: May 8, 2007

(54) METHOD OF SCREENING FOR SUBSTANCE PREVENTING OR TREATING DISEASES IN ASSOCIATION WITH MALFUNCTION OF IL-6 FAMILY CYTOKINE RECEPTOR MALFUNCTION

(75) Inventors: Toshio Hirano, 2-7-6, Anryu, Suminoe-ku, Osaka-shi, Osaka-fu (JP); Masahiko Hibi, Kobe (JP); Katsuhiko Ishihara, Ibaraki (JP)

(73) Assignees: Toshio Hirano, Osaka-fu (JP); Saten Pharmaceutical Co., Ltd., Osaka-fu (JP)

( * ) Notice: Subject to any disclaimer, the term of this patent is extended or adjusted under 35 U.S.C. 154(b) by 440 days.

(21) Appl. No.: 10/333,958

(22) PCT Filed: Jul. 27, 2001

(86) PCT No.: PCT/JP01/06464

§ 371 (c)(1),
(2), (4) Date: Jan. 27, 2003

(87) PCT Pub. No.: WO02/10749

PCT Pub. Date: Feb. 7, 2002

(65) Prior Publication Data
US 2004/0040045 A1 Feb. 26, 2004

(30) Foreign Application Priority Data
Jul. 28, 2000 (JP) ............................... 2000-229340

(51) Int. Cl.
*G01N 33/53* (2006.01)
*G01N 33/567* (2006.01)
(52) U.S. Cl. ................. 435/7.1; 435/7.21; 435/7.24
(58) Field of Classification Search .................. None
See application file for complete search history.

(56) References Cited

FOREIGN PATENT DOCUMENTS

JP 9-172908 7/1997

OTHER PUBLICATIONS

Voet et al. Biochemistry. John Wiley & Sons, Inc., pp. 126-128 and 228-234.*
Mikayama et al. Proc. Natl. Acad. Sci. USA vol. 90, pp. 10056-10060.*
Ohtani et al. Immunity, vol. 12, pp. 95-105, (2000).*
Cytokine & Growth Factor Review, vol. 8, No. 4, 1997, pp. 241-252, Hirano et al.
Proc. Natl. Acad. Sci., USA, vol. 94, No. 6, 1997, pp. 2478-2482, Kumanogoh et al.
Proc. Natl. Acad. Sci., USA, vol. 97, No. 12, 2000, pp. 6493-6498, Nicholson et al.
Biochemical Journal, vol. 335, No. 3, 1998, pp. 557-565, Schaper et al.
A. Timmermann et al., "Different epitopes are required for gp130 activation by interleukin-6, oncostatin M and leukemia inhibitory factor", FEBS Letters, vol. 468, No. 2-3, pp. 120-124, Feb. 25, 2000.
K. Ishihara et al., "The point mutation of tyrosine 759 of the IL-6 family cytokine receptor gp130 synergizes with HTLV-1 pX in promoting rheumatoid arthritis-like arthritis", International Immunology, vol. 16., No. 3, pp. 455-465, Mar. 2004.

* cited by examiner

*Primary Examiner*—Prema Mertz
(74) *Attorney, Agent, or Firm*—Wenderoth, Lind & Ponack, L.L.P.

(57) ABSTRACT

The invention provides a method of screening for substances preventing or treating diseases in association with IL-6 family cytokine receptor malfunction, which comprises using a transgenic mouse or a part thereof expressing a gp130 variant, wherein said gp130 variant comprises a substitution or a deletion of a tyrosine residue, which corresponds to the tyrosine residue at position 759 of human gp130 protein, or a substitution, an insertion or a deletion of one or more amino acid residues in a region comprising said tyrosine residue.

2 Claims, 7 Drawing Sheets

METHOD OF SCREENING FOR SUBSTANCE PREVENTING OR TREATING DISEASES IN ASSOCIATION WITH MALFUNCTION OF IL-6 FAMILY CYTOKINE RECEPTOR MALFUNCTION

This application is a U.S. national stage of International Application No. PCT/JP01/06464 filed Jul. 27, 2001.

TECHNICAL FIELD

The invention relates to a method of screening for substances preventing or treating diseases in association with malfunction of IL-6 family cytokine receptors, which comprise using of a transgenic mouse or a part thereof.

BACKGROUND ART

Rheumatoid arthritis (RA) is a chronic inflammatory disease accompanied with polyarthritis as a main lesion and a high prevalence of collagenosis (1% of the global population). Cause of the disease is unknown, but the disease is believed to be the result of environmental factors, such as infection, in addition to genetic factors. Correlation between development of symptom and HLA DR4 and the existence of T cells in synovial tissue suggest that abnormalities in T cells participate in the pathophysiology. Moreover, abnormalities in immunity, such as hyperglobulinemia due to polyclonal activation of B cells and appearance of autoantibodies, are observed. To date, model mice for autoimmune disease accompanied with arthritis and arthritis-induced model mice have been employed to analyze the pathophysiology of the disease, and transgenic mice and spontaneous mice which present arthritis have been reported in recent years. For example, the following are typical arthritis model mice reported to date.

1. Arthritis Model Mouse Induced by Antigenic Sensitization Etc.

The arthritis is induced by immunization of an intra-articular autoantigen with a strong adjuvant, or injection of microbial antigen crossreactive to the intra-articular autoantigen. Unlike RA, the symptoms are observed in a short period of time after the sensitization. The microbial antigen used is epidemiologically unrelated to human RA.

(1) Type II Collagen (IIC)-Induced Arthritis Model Mouse (Nature, 666–668, 1980. J. S. Courtenay et. al.)

Procedures: DBA/1J mouse is immunized with an emulsion prepared from bovine IIC and Freund's complete adjuvant. Three weeks later, bovine IIC and Freund's incomplete adjuvant are boosted, and the arthritis develops in 1–2 weeks.

Features: Unlike the adjuvant arthritis in rat, which is similar to Reiter's syndrome in human, this model is considered to be more relevant to human RA, in that it has no cutaneomucosa and organ involvement, and observations of the tissues resemble closely those in human RA. Cellular immunity and humoral immunity participate in this model mouse, and therefore, the arthritis can be induced with an anti-collagen monoclonal antibody. IL-6 is a precipitating factor (J. Exp. Med. 187, 461–468, 1998, Arthritis Rheumat. 42, 1635–1999). This model mouse is useful in producing various knock-out mice to identify gene products that aggravate or relieve arthritis.

Problems: Non-physiological operations for immunization are required. Deterioration-improvement pattern as observed in human RA is not observed. Rheumatoid factor (RF) is not produced.

(2) Antigen-Induced Arthritis Mouse (Arthritis Rheum. 20, 841–850, 1977)

Procedures: The arthritis is induced by sensitizing a mouse with an antigen, such as methylated bovine serum albumin, and followed by boosting of the antigen intra-articularly.

Features: IL-6 is a precipitating factor (Proc. Natl. Acad. Sci. USA, 95, 8222–8226, 1998). C57BL/6 and Balb/c mouse are used.

(3) CpG-Induced Arthritis Mouse (Nature Medicine, 5, 702–705, 1999, Arthritis Rheum. 43, 356–364, 2000)

Procedures: The arthritis is induced by intra-articular injection of CpG, which is a bacterial DNA having immuno-stimulating action.

Features: Macrophage precipitates in the arthritis. Local production of TNFα, IL-12, IL-1β, MCP-1, and RANTES in a joint, and increased production of blood IgG and IL-6 are involved. The arthritis can be induced in C57BL/6, Balb/c, C3H/HeN mouse, etc.

2. Spontaneous Arthritis Model Mouse (1) MRL-lpr/lpr and gld Mouse

Features: Abnormal proliferation of T cells, SLE-like lesion, arthritis and production of RF observed in this model are similar to those observed in human RA. It has been clearly shown that the main abnormalities are caused by Fas/Fas ligand.

Problems: Influences of a hereditary background involve symptoms that do not develop in C57BL/6, C3H, and AKR etc., and thus, development of the arthritis is not only due to abnormality in FAS/FAS ligand. Prolonged observation and analysis of progression of the disease are difficult, since the animal dies at about six-months old, because of abnormal multiplication of T cells.

(2) SKG Mouse (Reference: Molecular Medicine, vol 34, Extra Number, Immunity 1997–1998, p214–221)

Features: Symptoms of the arthritis are marked in comparison with MRL-lpr/lpr mouse. No abnormal proliferation of T cells is involved. Hyperglobulinemia is presented, and autoantibodies such as anti-IIC antibody and RF of IgM class are produced. The abnormalities in T cells are considered as the main cause because arthritis develops in a normal mouse by transplantation of T cells from a mouse presenting arthritis. This SKG mouse is derived from Balb/c mouse.

Problems: The cause of development of the disease is unknown.

3. Genetic-Engineering Model Mouse

Since the arthritis develops as a result of genetic engineering (gene transfer, knock-out, knock-in), the cause of development of the disease is clear.

(1) TNFα Transgenic Mouse (EMBO J. 10, 4025, 1991)

Features: This is a model mouse wherein the arthritis is caused by overproduction of cytokines. It has been shown that the arthritis is relieved with the anti-TNF antibody. In the hereditary background of DBA/1, the arthritis is more serious (J. Immunol. 159, 2867–2876, 1997). IL-1β and IL-6 are produced by cells in synovial membrane. The cells in synovium tissue are mainly neutrophils, and other fibroblasts and endothelial cells, and there is little participation of lymphocytes.

(2) HTLV-1Tax Transgenic Mouse (Science, 253, 1026–1028, 1991, J. Immunol, 155, 1588–1598, 1995, J. Immunol, 161, 6592–6598, 1998)

Features: Production of cytokines such as TNF, IL-1, and IL-6 are increased, because of the over-expression of Human T Cell Leukemia Virus Type 1 gene tax. Hyperglobulinemia is presented, and RF, anti-IIC and anti-DNA antibodies are produced. Development of symptoms is not related to H-2 haplotype. The incident is high in order of Balb/c, C3H/HeN, and C57BL/6.

(3) IL-1 Receptor Antagonist Knock-Out Mouse: (J. Exp. Med. 191, 313–320, 2000)

Features: The arthritis is developed in the hereditary background of Balb/c. The incident is low in C57BL/6. The arthritis develops, because of the deficiency of a molecule which negatively controls a citokine signal. Local production of IL-6 and IL-1β increases in a joint. Hyperglobulinemia is presented, and RF, anti-IIC and anti-DNA antibodies are produced.

(4) T Cell Antigen Receptor Transgenic Mouse (Cell, 87, 811–822, 1996, Immunity 10, 451–461, 1999, Science, 286, 1732–1735, 1999)

Features: A transgenic mouse, which has a T cell receptor (α, β) that I-Ak-restrictively recognizes bovine pancreas ribonuclease peptide R41-61, is crossed with a NOD mouse to develop arthritis. Neutrophilic infiltration is observed in a joint space. Hyperglobulinemia and anti-DNA antibodies are observed, but RF is not observed. The arthritis is possible to be developed in a healthy mouse with introduction of the antibody in the serum of a mouse presenting arthritis, and it has been shown clearly that the antigen, which is recognized by this antibody and T cells of the mouse presenting arthritis, is such antigen as referred to as Glucose-6-Phosphate Isomerase (GPI). It is associated with mechanisms wherein ribonuclease-specific T cells recognize GPI combined with I-Ag7 inherent in NOD mouse and are activated to induce a inflammatory response specific to a join.

The model mice described above present the symptoms of arthritis by the mechanisms that are respectively different, such that they reflect that the pathogenesis of human RA, which is caused by many factors. Although all pathophysiology shown in these model mouse are not completely consistent with those in human RA, it is apparent that a new arthritis model mouse would be useful in analysis of a certain aspect of the onset of RA, in view of the fact that multiple factors participate in development of RA.

Participation of IL-6 in the pathophysiology of arthritis has been shown not only by clinical observations, but also in the model mice described above. However, there is no case wherein the arthritis is actually developed in any IL-6 related genetic mouse reported to date. Moreover, although it has been produced by many model mice presenting arthritis, which have been gene-engineered to enhance the production of cytokines and their function, there are few among these model mice that are suitable for analysis of the functional abnormalities of T cells. The T cell antigen receptor transgenic mouse described above could not demonstrate how self-reactivity T cell clones are selected from the T cell repertories to break the self-tolerance. Although abnormalities such as T cell selection may participate in SKG mouse, it is difficult to investigate the cause of the disease because of spontaneous development of the symptoms.

gp130 is a membrane protein having a molecular weight of 130 kDa and a common receptor subunit for L-6 family citokines. gp130 participates in not only IL-6 signal transmission but also signal transmissions of other IL-6 family citokines: leukemia inhibitory factor (LIF), ciliary neurotrophic factor (CNTF), oncostatin M (OSM), Interleukin-11 (IL-11), and cardiotrophin-1 (CT-1). (Hirano, T. et al. (1997) Cytokine Growth Factor Rev. 8, 241–52).

IL-6 family cytokine binds to a receptor, and thereby homodimer formation between gp130 proteins or heterodimer formation between gp130 protein and another gp130 related factor is induced. Subsequently, a tyrosine residue on the gp130 protein is phosphorylated, and SHP2 (SH2 domain contained protein tyrosine phosphoatase 2) is associated with the phosphorylated tyrosine residue, and the SHP2 is further phosphorylated to transmit signals downstream. The phosphorylation of SHP2 necessitates phosphorylation of tyrosine 759 in human gp130 (Hirano, T. et al. (1997) Cytokine Growth Factor Rev. 8, 241–52). Furthermore, it was reported recently that the molecule called SOCS-3 (suppressor of cytokine signaling-3), which is responsible for feedback control of the cytokine signal, binds to this tyrosine 759 of human gp130 protein (Proc. Natl. Acad. Sci. USA, 2000, 97, 6493–8).

The amino acid sequence of human gp130 protein is known, and cDNA encoding the human gp130 protein has been reported (Hibi, M et al., (1990) Cell 63, 1149–57). Also, the amino acid sequence of mouse gp130 is known, and cDNA encoding the mouse gp130 has been reported (Saito et al., (1992) J. Immunol. 148, 4066–71).

DISCLOSURE OF INVENTION

The present invention provides a screening method utilizing a new pathologic model for substances preventing or treating diseases in association with malfunction of IL-6 family cytokine receptor.

The present invention is based on the discovery that a transgenic mouse, wherein SHP2-mediated gp130-dependent signaling cascade is selectively disrupted, exhibits symptoms characteristic in autoimmune disease, arthritis and rheumatoid arthritis as the result of malfunction of IL-6 family cytokines.

Thus, the present invention provides

1) A method of screening for substances preventing or treating diseases in association with IL-6 family cytokine receptor malfunction, which comprises using a transgenic mouse or a part thereof expressing a gp130 variant, wherein said gp130 variant comprises a substitution or a deletion of a tyrosine residue, which corresponds to the tyrosine residue at position 759 of human gp130 protein, or a substitution, an insertion or a deletion of one or more amino acid residues in a region comprising said tyrosine residue;

2) A method of screening for substances preventing or treating autoimmune diseases, which comprises using a transgenic mouse or a part thereof expressing a gp130 variant, wherein said gp130 variant comprises a substitution or a deletion of a tyrosine residue, which corresponds to the tyrosine residue at position 759 of human gp130 protein, or a substitution, an insertion or a deletion of one or more amino acid residues in a region comprising said tyrosine residue;

3) A method of screening for substances preventing or treating arthritis, which comprises using a transgenic mouse or a part thereof expressing a gp130 variant, wherein said gp130 variant comprises a substitution or a deletion of a tyrosine residue, which corresponds to the tyrosine residue at position 759 of human gp130 protein, or a substitution, an insertion or a deletion of one or more amino acid residues in a region comprising said tyrosine residue;

4) A method of screening for substances preventing or treating rheumatoid arthritis, which comprises using a transgenic mouse or a part thereof expressing a gp130 variant, wherein said gp130 variant comprises a substitution or a deletion of a tyrosine residue, which corresponds to the tyrosine residue at position 759 of human gp130 protein, or a substitution, an insertion or a deletion of one or more amino acid residues in a region comprising said tyrosine residue;

5) A method of screening for antiinflammatory drugs, which comprises using a transgenic mouse or a part thereof expressing a gp130 variant, wherein said gp130 variant comprises a substitution or a deletion of a tyrosine, which corresponds to the tyrosine residue at position 759 of human gp130 protein, or a substitution, an insertion or a deletion of one or more amino acid residues in a region comprising said tyrosine residue;

6) The method of screening according to any one of claims 1–5, wherein the SHP2-mediated gp130-dependent signaling cascade is selectively disrupted in said transgenic mouse or a part thereof expressing a gp130 variant;

7) The method of screening according to any one of claims 1–5, wherein the negative regulation by SOCS-3 of the gp130-dependent signaling cascade is disrupted in said transgenic mouse or a part thereof expressing a gp130 variant.

8) The method of screening according to any one of claims 1–7, wherein said gp130 variant comprises a substitution or a deletion of a tyrosine residue, which corresponds to the tyrosine residue at position 759 of human gp130 protein.

9) The method of screening according to claim 8, wherein said substitution of a tyrosine residue, which corresponds to the tyrosine residue at position 759 of human gp130 protein, is the result of a point mutation of the gp130 gene; and 10) The method of screening according to claim 9, wherein phenylalanine is encoded in place of tyrosine as the result of said point mutation.

The disease which develops in the transgenic mouse of the invention appears to be caused by not only selective disruption of the SHP2-mediated gp130-dependent signaling cascade, but also malfunction of feedback control of the cytokine signalling by binding of SOCS-3. Moreover, any other unknown signaling molecule requiring tyrosine 759 of human gp130 (or any tyrosine residue corresponding thereto) might participate in development of the disease in the transgenic mouse of the invention. The diseases which develop in the transgenic mouse of the invention appear to be caused by one or more of these unknown signaling molecules which do not work.

Considering that there is no case wherein arthritis has actually presented, the inventors' knowledge that arthritis is caused by a point mutation in a gene for gp130, which is a common receptor subunit for IL-6 family cytokines, which provides valuable information. Moreover, based on the inventors' findings that a cytokine receptor simultaneously transmits not only multiple signals, but also sometimes signals opposing each other, the transgenic mouse of the invention would be a unique model mouse demonstrating that the disease can be caused by only disruption of the balance of these multiple signals.

Furthermore, it would be likely that some of the actual cases of RA related diseases had been caused in the similar manner as in the transgenic mouse of the invention, considering that the transgenic mouse could present arthritis with only a point mutation. Moreover, considering that arthritis could be caused by transplantation of spleen cells of the transgenic mouse of the invention into a lymphocyte-deficient RAG2 knock-out mouse, and that living/proliferation of the activated CD4+ T cells is observed in this RAG2 knock-out mouse, the arthritis developed in the transgenic mouse of the invention is likely caused by abnormalities in immunity principally involved with T cells. Indeed, this is suggested from the fact that T cells expressing both CD4 and CD8 (i.e., CD4/CD8 double positive cell) decrease and T cells expressing CD4 alone (i.e., CD4 single positive cell) increase in the thymus of the transgenic mouse of the invention, and that CD4+ T cells expressing activated antigens on their surfaces increase in the thymus and peripheral lymphocytes.

BRIEF DESCRIPTION OF DRAWINGS

FIG. 7 shows the results of flow cytometry analysis of a thymus of gp130$^{F759/F759}$ mouse. Thymus cells of a mouse were multiply stained with a fluorescence-labeled monoclonal antibodies, and the fluorescence intensities were measured by flow cytometer. Vertical and lateral axes indicate the fluorescence intensities reflecting the binding of the fluorescence-labeled antibodies against the surface antigens, which are indicated in the vertical and lateral direction on the left side of the panels, respectively, and thus, the expression levels of the surface antigens are indicated for the individual cells. Upper panels: the results of analysis of CD4 and CD8 expressions. Lower panels: the results of analysis of IgD and IgM expressions. Left panels (WILD/F759) show the results of control mouse (gp130$^{WT/F759}$ mouse) and right panels (F759/F759) show the results of gp130$^{F759/F759}$ mouse. The numbers in the panels indicate the frequency (%) of the cell population within areas boxed or separated by cross lines.

FIG. 8 shows the results of flow cytometry analysis of a lymph node of gp130$^{F759/F759}$ mouse. Lymph node cells of a mouse were multiply stained with fluorescence-labeled monoclonal antibodies, and the fluorescence intensities were measured by flow cytometer. Vertical and lateral axes indicate the fluorescence intensities reflecting the binding of the fluorescence-labeled antibodies against the surface antigens, which are indicated in the vertical and lateral direction on the left side of the panels, respectively, and thus, the expression levels of the surface antigens are indicated for the individual cells. Upper panels: the results of analysis of CD4 and CD8 expressions. Middle panels: the results of analysis of IgD and IgM expressions. Lower panels: the results of analysis of Gr-1 and CD11 expressions. Left panels (WILD/F759) show the results of control mouse (gp130$^{WT/F759}$ mouse) and right panels (F759/F759) show the results of gp130$^{F759/F759}$ mouse. The numbers in the panels indicate the frequency (%) of the cell population within areas boxed or separated by cross lines.

FIG. 9 shows the results of flow cytometry analysis of CD4 and CD8 single positive cells in a lymph node of gp130$^{F759/F759}$ mouse. CD4 or CD8 single positive cells in a lymph node of a mouse were multiply stained with a fluorescence-labeled monoclonal antibodies, and the fluorescence intensities were measured by flow cytometer. Vertical and lateral axes indicate the fluorescence intensities reflecting the binding of the fluorescence-labeled antibodies against the surface antigens, which are indicated in the vertical and lateral direction on the left side of the panels, respectively, and thus, the expression levels of the surface antigens are indicated for the individual cells. Upper panels: the results of analysis of CD69 and CD25 expressions in CD4 single positive cells. Middle panels: the results of analysis of CD62L and CD44 expressions in CD4 single positive cells. Lower panels: the results of analysis of CD62L and CD44 expressions in CD8 single positive cells. Left panels (WILD/F759) show the results of control mouse (gp130$^{WT/F759}$ mouse) and right panels (F759/F759) show the results of gp130$^{F759/F759}$ mouse. The numbers in the panels indicate the frequency (%) of the cell population within areas boxed or separated by cross lines.

BEST MODE FOR CARRYING OUT THE INVENTION

The term "tyrosine residue corresponding to the tyrosine residue at position 759 of human gp130 protein" as used herein means a tyrosine residue in gp130 protein of the transgenic mouse of the invention, wherein said tyrosine residue corresponds to the tyrosine residue located at position 759 in human gp130 protein. The term "region comprising a tyrosine residue corresponding to the tyrosine residue at position 759 of human gp130 protein" means a region of the amino acid residues in the gp130 protein of the transgenic mouse of the invention, wherein said region comprises said tyrosine residue corresponding to the tyrosine residue at position 759 of human gp130 protein. In a gp130 variant expressed in the transgenic mouse of the invention, a tyrosine residue, which corresponds to the tyrosine residue at position 759 of human gp130 protein, is substituted or deleted, and/or one or more amino acid residue are substituted, inserted or deleted in a region comprising said corresponding tyrosine residue.

gp130 variant expressed in the transgenic mouse which is used in the method of screening of the invention may also have any mutation so that the functions of any other unknown signaling molecule, which requires a tyrosine residue corresponding to the tyrosine at position 759 of human gp130 protein as well as the bindings of SHP2 and SOCS-3, can be inhibited. Thus, in the transgenic mouse used in the screening method of the invention, the SHP2-mediated gp130-dependent signaling cascade is selectively disrupted, the feedback control of cytokine signaling by binding of SOCS-3 does not work, and the functions of any unknown signaling molecule requiring a tyrosine residue, which corresponds to the tyrosine residue at position 759 of human gp130 protein, are inhibited.

In the present invention, gp130 variant expressed in the transgenic mouse of the invention comprises substitution, insertion, or deletion of one or more amino acid residues in a region comprising a tyrosine residue, which corresponds to the tyrosine residue at position 759 of human gp130 protein. The tyrosine residue itself, which corresponds to the tyrosine residue at position 759 of human gp130 protein, may be or not be substituted, so long as the functions of the signaling molecule requiring said tyrosine residue are inhibited.

In a preferred embodiment of the invention, gp130 variant expressed in the transgenic mouse of the invention comprises substitution or deletion of a tyrosine residue, which corresponds to the tyrosine residue at position 759 of human gp130 protein.

In a more preferred embodiment of the invention, gp130 variant expressed in the transgenic mouse of the invention comprises substitution of a tyrosine residue, which corresponds to the tyrosine residue at position 759 of human gp130 protein, by a point mutation of the gp130 gene.

The term "point mutation" refers to a mutation whereby a single base pair on a DNA molecule is substituted with any different base pair. The point mutation may be directly introduced into the gp130 gene in mouse genome, or introduced by homologous recombination between a fragment of mutant gp130 gene containing such point mutation and the gp130 gene of mouse genome. The point mutation specifically preferable in the method of the invention is, for example, such point mutation as phenylalanine is encoded. As used herein, the transgenic mouse wherein a mutant gp130 gene having such point mutation is introduced is referred to as "gp130$^{F759}$ mouse", and a homozygote of the mutant gp130 gene is especially referred to as "gp130$^{F759/F759}$ mouse". Further, a heterozygote between the wild-type gp130 gene and the mutant gp130 gene is referred to as "gp130$^{WT/F759}$ mouse", and a homozygote of the wild-type gp130 gene is referred to as "gp130$^{WT/WT}$ mouse".

The transgenic mouse used in the screening method of the invention may be prepared in the following manner. A mutant gp130 gene is prepared by direct introduction of the above mutation into the gp130 gene of mouse or by homologous recombination between the fragment of mutant gp130 gene as described above and the gp130 gene of mouse genome, and the mutant gp130 gene obtained is then introduced into a mouse ES cell using procedures well known in the art to establish an ES cell comprising mutations on the gp130 genome. Then, the ES cells is introduced into a blastocyst cell taken from another mouse, the blastocyst cell is introduced into a uterus of a pseudopregnant mouse, and a chimeric mouse born of the pseudopregnant mouse and a wild-type mouse are crossed to produce the first generation of heterozygous mice. The heterozygous mice of the first generation are then crossed with each other to produce the second generation of homozygous mice. The transgenic mouse used in the screening method of the invention may be prepared, for example, according to the procedures described in Immunity, Vol. 12, 95–105, January, 2000.

A test compound which may be used in the screening method of the invention includes, for example, peptides, proteins, non-peptide compounds, antisense DNAs, antisense RNAs, synthetic compounds, fermented products, cell extracts, plant extracts, mammal tissue extracts, plasma, serum and the like, and these test compounds may be novel or known.

The means for administration of a test compound in the screening method of the invention includes, for example, oral administration, intravenous injection, intradermal injection, intramuscular injection and the like. Those skilled in the art can appropriately select the dosage of a test compound according to the route of administration, the property of the test compound and the like. The administration of a test compound may be started prior to the timing of the onset of immune abnormality or the disease for screening of prophylactic drugs, whereas after the disease is macroscopically presented for screening of therapeutic agents.

In the screening method of the invention, male and female wild and the transgenic mice of the invention are divided into groups, and the animals, with or without administration of a test compound, are visually observed and scored for the severity of the symptom. Blood was collected from the mice and subjected to blood cell counting and serological a test, additionally a urine test and the like are also conducted. After a certain period of observation, X-ray photogram analysis, pathological analysis and immunological analysis are conducted. If any mouse died from unknown cause during the test period, pathological autopsy is conducted to clarify the cause.

Tissues or cells are isolated from the transgenic mouse of the invention and subjected to analyses in vitro to assess preventing or therapeutic effect of a test compound, changes in the cellular phenotype resulting from the genetic modification for changes in cell growth and cytokine production and the like.

Further, the transgenic mouse of the invention may be crossed to produce various mice of different genetic backgrounds, so that it is possible to assess influences in development of the diseases and to try various induced model mice to establish experimental systems permitting more rapid screenings for preventing agents or therapeutic agents.

The examples described below should be construed to illustrate the present invention, and not to limit the scope of the invention in any way.

EXAMPLES

Preparation of gp130$^{F759/F759}$ Mouse

In accordance with the method as described in *Immunity*, Vol. 12, 95–105, January, 2000, the EcoRI-XhoI fragment of human gp130 cDNA containing the point mutation that is a substitution of tyrosine 759 with phenylalanine (mutation from TAT to TTT) (Yamanaka, Y et al. (1996) EMBO J. 15, 1557–65), wherein the XhoI site was created by the subcloning, was introduced into mouse gp130 gene to provide mouse-human chimeric gp130 constructs. The targeting vectors bearing the constructs were transduced into mouse ES cells by electroporation, and the ES cells containing the mutation in gp130 genome were established. Using the microinjection method, the transgenic ES cells were injected into blastocysts that had been taken from C57BL/6 mice. The blastocysts injected with the ES cells were transplanted into a uterus of a pseudopregnant mouse (ICR line) as obtained by intercoursing with a mouse subjected to vasoligation. Chimeric mice of the newborns from the pseudopregnant mouse were crossed with C57BL/6 wild-type mice to provide the first generation hetero mice. Crossing between the first generation hetero mice provided the second generation homozygous mice (gp130$^{F759/F759}$ mice).

Analysis for Pathophysiology of gp130$^{F759/F759}$ Mouse

Figure 1:
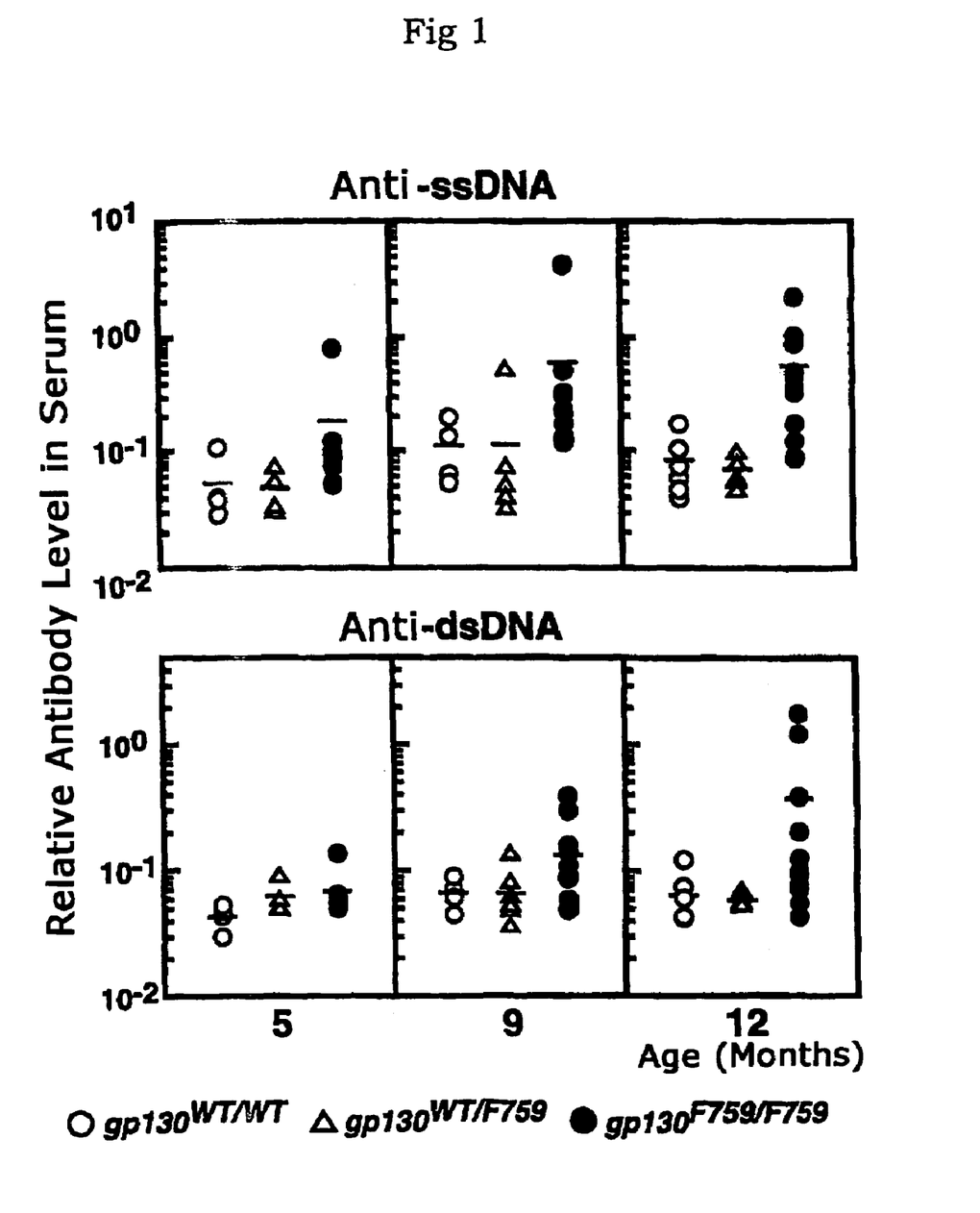
FIG. 1 shows antibody levels of the anti-ssDNA antibody and the anti-dsDNA antibody in mice at 12 months of age. Open circle: gp130$^{WT/WT}$ mouse (n=6), triangle: gp130$^{WT/F759}$ mouse (n=5), closed circle: gp130$^{WT/WT}$ mouse (n=11). Horizontal bars indicate the mean values.

Production of autoantibodies:

Blood was collected from gp130$^{F759/F759}$ mice at the age of 5, 9 and 12 months, and the serums were separated. Production levels of autoantibodies such as immunoglobulin, anti-ssDNA (single-stranded DNA)-, anti-dsDNA (double-stranded DNA)-, anti-nRNP (ribonucleoprotein)-antibodies, and rheumatoid factors were determined by ELISA method. The productions of autoantibodies such as anti-ssDNA- and anti-dsDNA-antibodies were found in the mice aged 9 months and more. The results of the determinations in the mice at the age of 5, 9 and 12 months are shown in FIG. 1.

Figure 2:
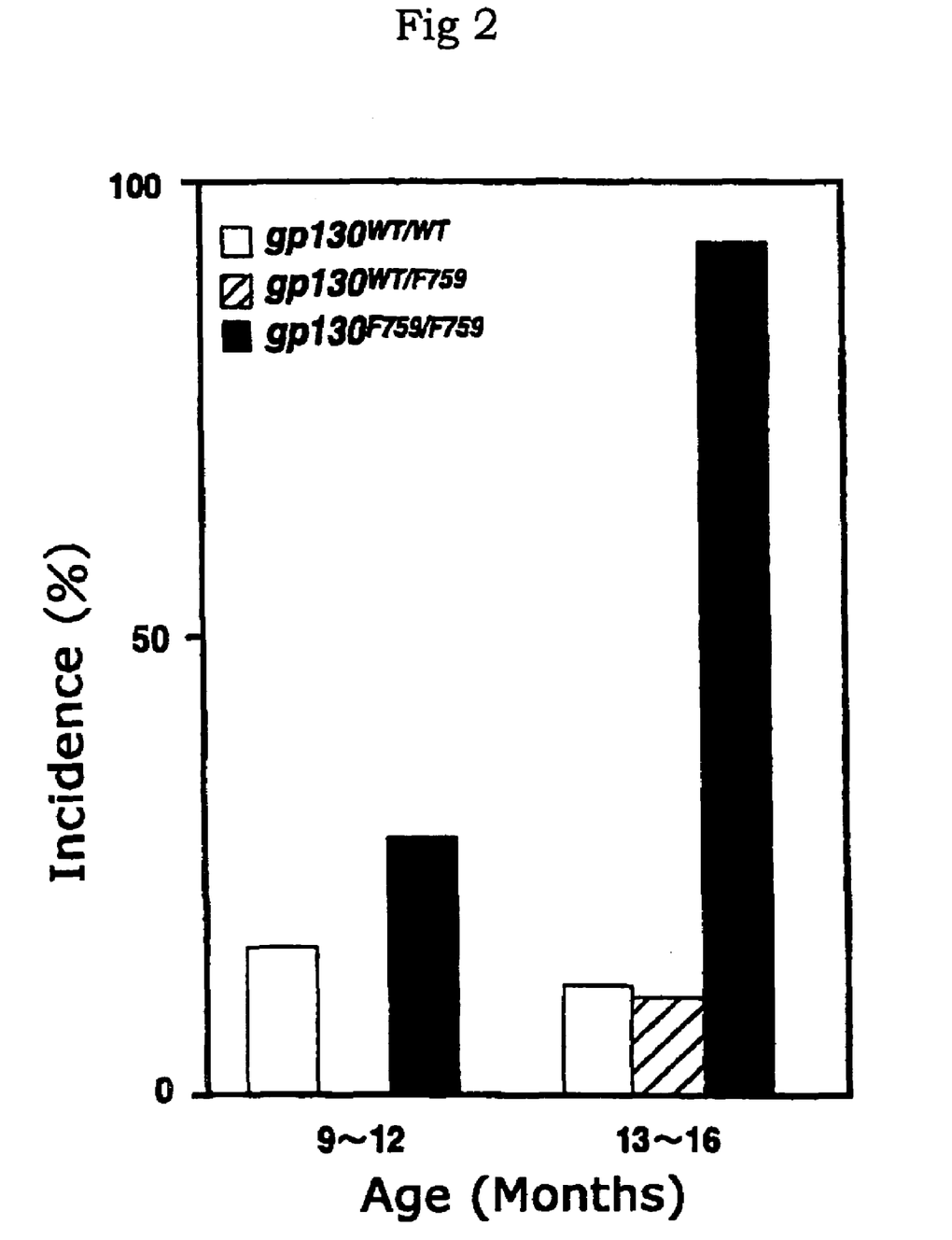
FIG. 2 shows incidences of arthritis in mice.
Figure 3:
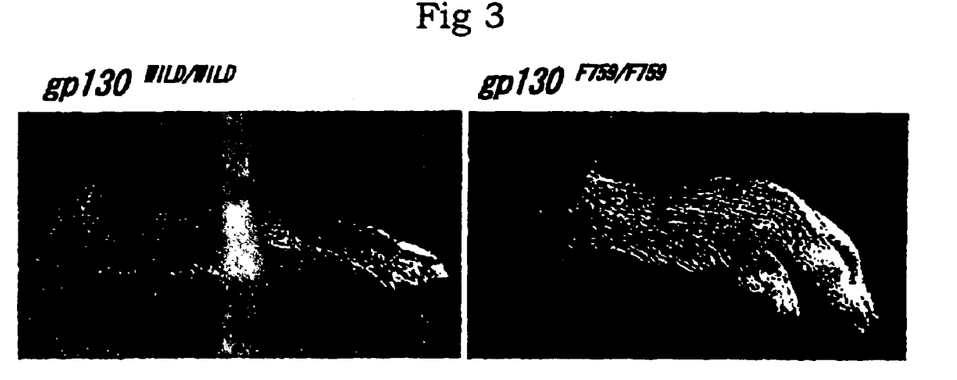
FIG. 3 is macroscopic observation of arthritis in gp130$^{F759/F759}$ mouse (a copy of ankle photograph of a 9.5-month-old mouse). Left: ankle of control mouse (gp130$^{WT/WT}$ mouse). Right: ankle of gp130$^{F759/F759}$ mouse.
Figure 4:
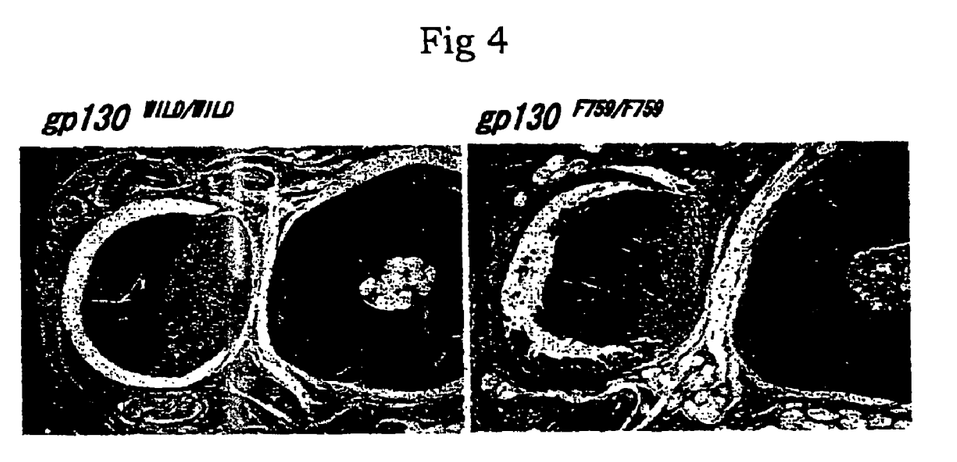
FIG. 4 shows pathological pictures of an ankle of gp130$^{F759/F759}$ mouse (15-month-old: hematoxylin-eosin stain of synovial tissue (×40)). Left: control mouse (gp130$^{WT/WT}$ mouse). Right: gp130$^{F759/F759}$ mouse. The arrowhead indicates fibroblasts growth, and the arrow indicates neutrophilic infiltration.
Figure 5:
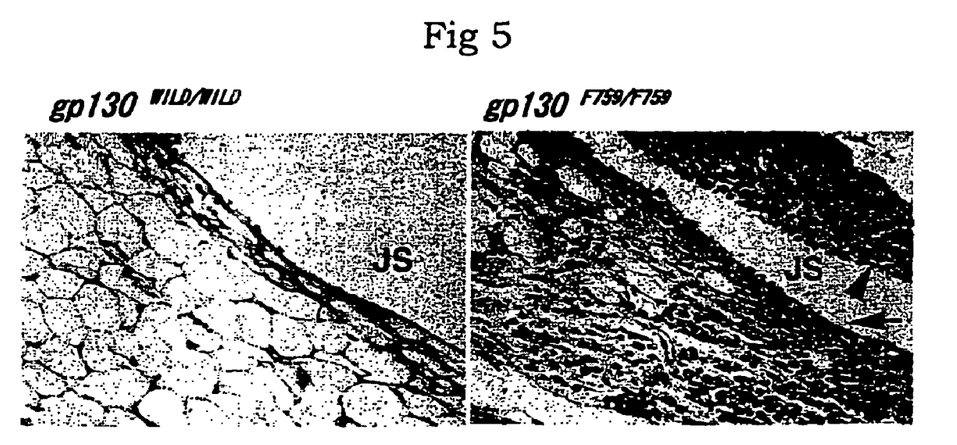
FIG. 5 shows pathological pictures of a knee joint of gp130$^{F759/F759}$ mouse (15-month-old: hematoxylin-eosin stain of synovial tissue (×100)). Left: control mouse (gp130$^{WT/WT}$ mouse). Right: gp130$^{F759/F759}$ mouse. JS: joint space. The arrowhead indicates neutrophilic infiltration accompanied with fibrin deposition, and the arrow indicates thickening of synovial tissue accompanied with neutrophilic infiltration and fibroblasts growth.
Figure 6:
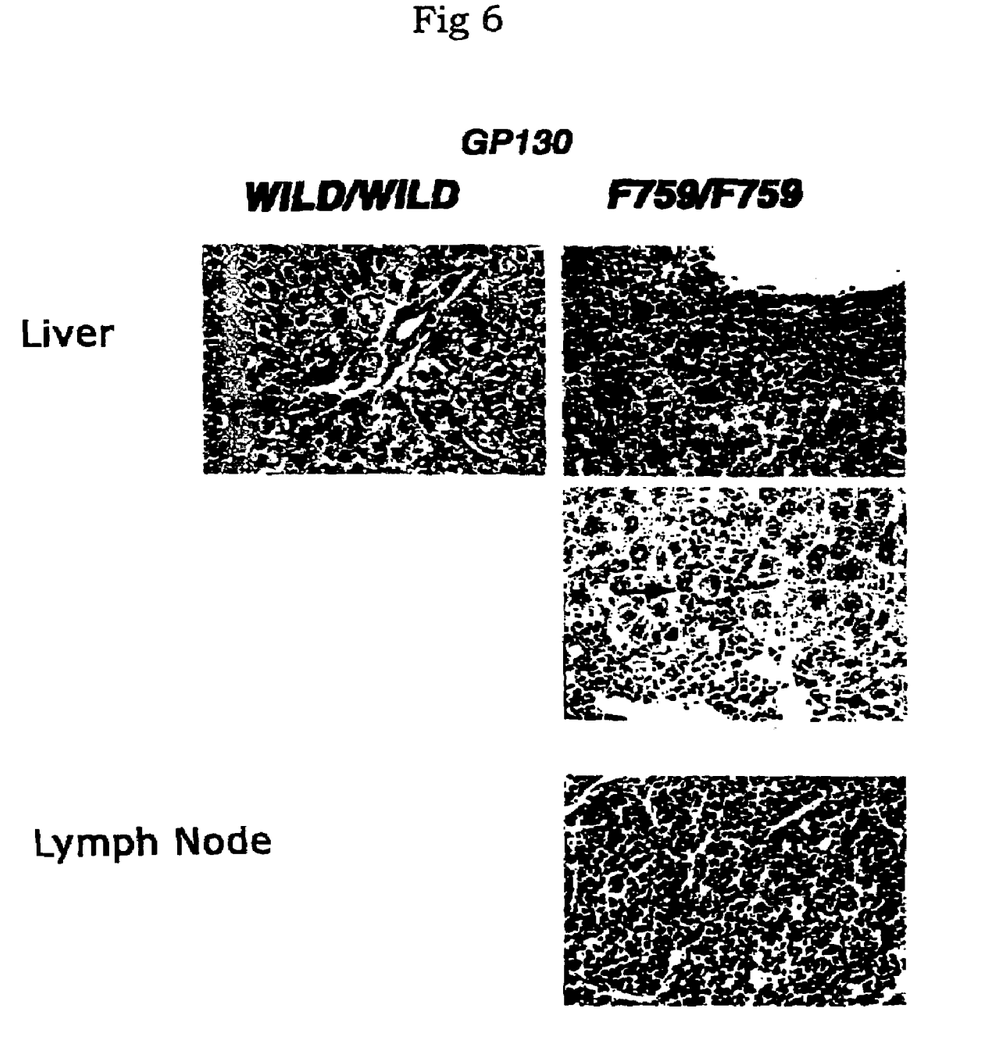
FIG. 6 shows pathological pictures of a liver of gp130$^{F759/F759}$ mouse (hematoxylin-eosin stain of synovial tissue (×100)). Left upper: liver of control mouse (gp130$^{WT/F759}$ mouse) (9.5-month-old). Right upper: liver of gp130$^{F759/F759}$ mouse (9.5-month-old). Right middle: liver of gp130$^{F759/F759}$ mouse (15.5-month-old). The arrow indicates degeneration of hepatocytes. Right lower: lymph node of gp130$^{F759/F759}$ mouse (15.5-month-old).

Development of arthritis:

gp130$^{F759/F759}$ mice were observed for the development of arthritis until 20 months after birth. Twenty % of the gp130$^{F759/F759}$ mice aged 8–10 months developed arthritis, whereas the gp130$^{F759/F759}$ mice aged 20 months developed arthritis at near 100% (FIG. 2). FIG. 3 shows the macroscopic observation of the arthritis in the gp130$^{F759/F759}$ mice (aged 9.5 months). In the gp130$^{F759/F759}$ mice, the swelling and the restricting range of motion in the proximal finger joints of the extremities were found, and the arthritis attacked even the major joints, then causing the ankylosing changes. After the gp130$^{F759/F759}$ mice that developed arthritis were sacrificed, the joints, the thymus gland, the spleen, the liver or the lymph node was removed, and fixed on formalin. Then, the pathological samples were prepared according to conventional manners, stained with hematoxylin and eosin, and subjected to the pathological examination with an optical microscope. FIGS. 4–6 show the results of the histopathological examination of the gp130$^{F759/F759}$ mice. The gp130$^{F759/F759}$ mouse were outstanding in fibrin deposition, neutrophilic infiltration, and joint structure destruction associated with fibroblasts growth in the synovial membrane (FIGS. 4 and 5). Further, plasma cell infiltration around the Glisson's capsule of the liver (9.5-month-old: the right upper in FIG. 6), and the hepatic cell degeneration (15.5-month-old: the right medium in FIG. 6) were observed. Also, plasma cell infiltration in the lymph node was observed (the right lower in FIG. 6).

Figure 7:
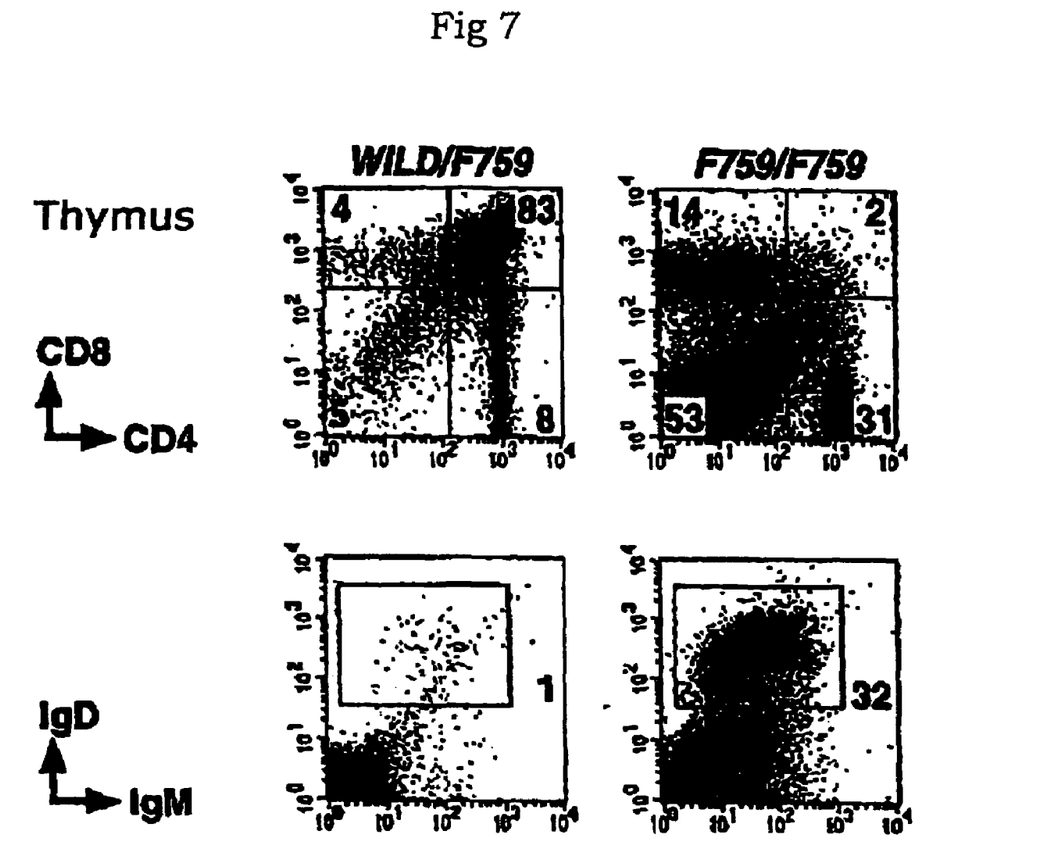
Figure 8:
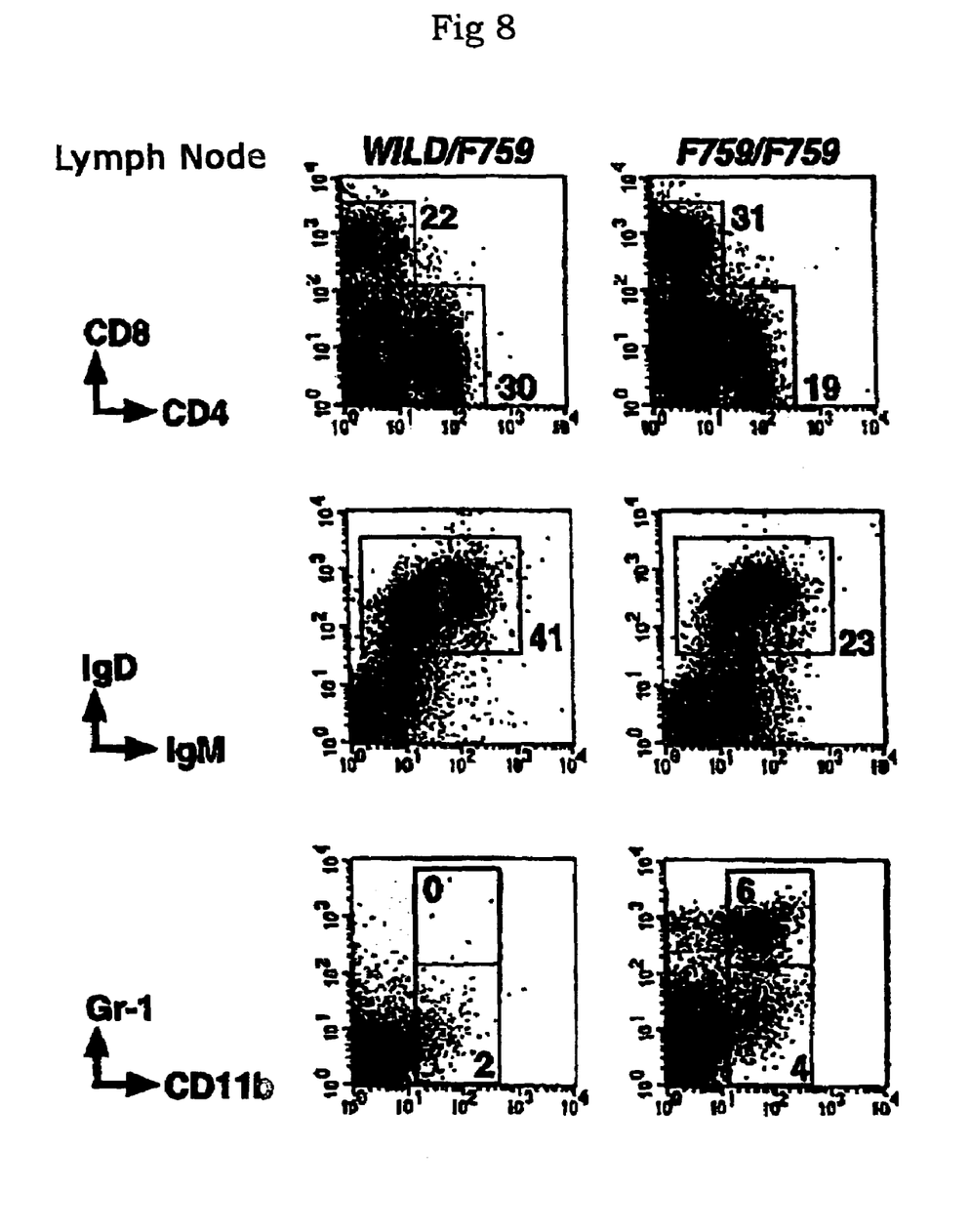
Figure 9:
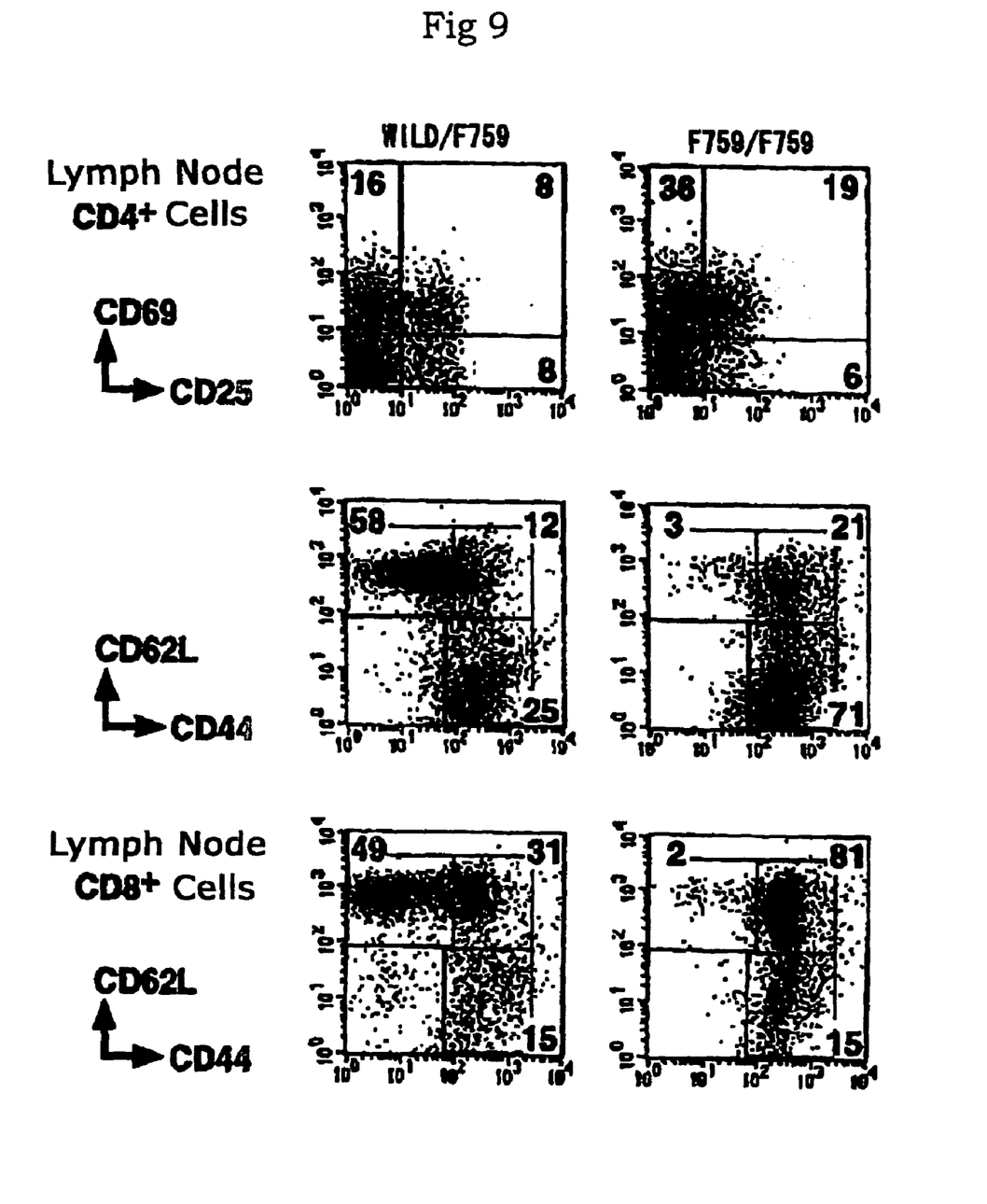

Aberrations in lymphatic tissues (analysis by flow cytometry):

Cells were removed from the lymphatic tissues (thymic gland and lymph node), and were examined for the cell surface markers and antibodies to each specific surface antigens with a cell surface analyzer. In the thymic gland, T cells expressing both CD4 and CD8 (CD4/CD8 double-positive T cells) were decreased (2% in the gp130$^{F759/F759}$ mice, whereas 83% in the control: the upper in FIG. 7), and T cells expressing singly either CD4 or CD8 (CD4 single-positive T cells, CD8 single-positive T cells) were increased (31% and 14% in the gp130$^{F759/F759}$ mice, respectively, whereas 8% and 4% in the control: the upper in FIG. 7). Further, unusual proliferation of B cell (IgD+IgM$^{lo}$ (lower expression of IgM)) was observed in the thymic gland of the gp130$^{F759/F759}$ mice (32% increase: the lower in FIG. 7), which was not found in normal thymic gland. In the lymph node of the gp130$^{F759/F759}$ mice, Gr-1+CD11b+ granulocytes were increased (6%: the lower in FIG. 8). Additional examination on the CD4 single-positive T cells in the lymph node of the gp130$^{F759/F759}$ mice revealed that the cells positive at marker CD69 or CD25 indicate that activated cells were increased (the upper in FIG. 9). Examination on the CD62L and CD44 expressions revealed that there was a decrease in naive T cells (CD62L+CD44−) (3% in the gp130$^{F759/F759}$ mice, whereas 58% in the control), and the increase in activated memory T cells (CD62L−CD44+) (71% in the gp130$^{F759/F759}$ mice, whereas 25% in the control) were observed among the CD4 single-positive T cells in the lymph node of the gp130$^{F759/F759}$ mice (the medium in FIG. 9). Among the CD8 single-positive cells, the decrease in naive T cells (CD62L+CD44−) 2% in the gp130$^{F759/F759}$ mice, whereas 49% in the control: the lower in FIG. 9) was observed. These results show that the T cells in the lymph node were unusually activated in the gp130$^{F759/F759}$ mice, which developed the arthritis.

Test Example 1

Screening Test for Anti-Arthritis Agents gp130$^{F759/F759}$ mice or mice obtained by backcrossing of the gp130$^{F759/F759}$ mice (gp130$^{F759/F759}$-related mice) were used as a model mouse. A test compound of antirheumatic drugs such as bucilamine and methotrexate, nonsteroidal anti-inflammatory drugs such as diclofenac, or steroidal drugs such as dexamethasone was administered. The administration was conducted before the onset of immune disorders or arthritis for screening of prophylactic drugs, whereas after the observation of visible arthritis for screening of therapeutic drugs. The following is to illustrate the screening test for anti-arthritic agents using methotrexate as a test compound, and screening tests for other compounds would be conducted according to a similar manner to the following.

Methotrexate was administered orally at a dose of 0.4 mg/kg to the mice at the aged of 9 months for five days in a week. Male or female wild or gp130$^{F759/F759}$ mice were divided into groups of 2 or 3 animals per group, which were observed with naked eye for the course of the prophylactic or therapeutic effect on the arthritis. The severity of arthritis was scored based on restricted range of motion, swelling and flare of digit joints, and the presence or absence of rigidity. The mice whose arthritis conditions were observed constantly for two weeks or more were estimated as developed animal, and incident and severity were determined with time course.

Consequently, in the control (without methotrexate), the animals at the age of 40 weeks or older (about 10-month-old) were found to have the arthritis, and all of the animals aged 46 weeks developed the arthritis. Further estimation of the arthritis score in the mice developing arthritis with time course revealed that the animals aged 48 weeks (12-month-old) and 53 weeks in the group receiving methotrexate (0.4 mg/kg) showed 1.33±0.33 and 0.67±0.33, respectively, whereas the animals aged 48 weeks (12-month-old) and 53 weeks in the control showed 4.33±1.86 and 4.67±0.67, showing that methotrexate inhibits the arthritis in the mouse model of the present invention.

Test Example 2

Screening Test for Anti-Inflammatory Drugs

Using gp130$^{F759/F759}$ mice or their related mice, the air pouch model is prepared to screen for a compound having an inflammatory activity. Candidate compounds possibly having an inflammatory activity are administered to the air pouch model as prepared according to a conventional manner before or after inducing inflammation, and the infiltrations of neutrophil and macrophage in the air pouch are examined. Further, the changes in phenotypes in gp130$^{F759/F759}$ mice caused by other inflammatory-inducing agents are examined in a similar manner to the method of Test Example 1.

Test Example 3

Screening Test for Antiinfection Drugs gp130$^{F759/F759}$ mice are so sensitive to listeriosis that they are often die due to the infection. Accordingly, gp130$^{F759/F759}$ mice can be used to screen for a compound having a therapeutic activity for infections. For example, the mice are infected with *Listeria*, a test compound is administered thereto, and the therapeutic effect is examined using survival rate as an index.

Test Example 4

Screening Test for Drugs Controlling an IL-6-Family Cytokine Signal.

It is believed that gp130$^{F759/F759}$ mice would develop diseases caused by overexpression of STAT3 that involves signal transmission mediated by IL-6. Accordingly, gp130$^{F759/F759}$ mice can be used to screen for a compound that prevent or treat diseases caused by aberration in signal transmission mediated by IL-6. The tissues, the cells, the genes or the proteins derived from the mice are also used to screen for various drugs that control the signal.

The invention claimed is:

1. A method of screening for substances for treating arthritis in association with IL-6 family cytokine receptor malfunction, said method comprises using a transgenic mouse expressing a gp130 variant, wherein said gp130 variant comprises a substitution, which corresponds to the tyrosine residue at position 759 of human gp130 protein, in which the tyrosine is substituted by a phenylalanine.

2. A method of screening for substances for treating rheumatoid arthritis in association with IL-6 family cytokine receptor malfunction, said method comprises using a transgenic mouse expressing a gp130 variant, wherein said gp130 variant comprises a substitution, which corresponds to the tyrosine residue at position 759 of human gp130 protein, in which the tyrosine is substituted by a phenylalanine.

* * * * *

UNITED STATES PATENT AND TRADEMARK OFFICE
CERTIFICATE OF CORRECTION

PATENT NO. : 7,214,494 B2  
APPLICATION NO. : 10/333958  
DATED : May 8, 2007  
INVENTOR(S) : Toshio Hirano et al.

Page 1 of 1

It is certified that error appears in the above-identified patent and that said Letters Patent is hereby corrected as shown below:

ON THE TITLE PAGE:
Item (73) Assignees:

"Toshio Hirano, Osaka-fu (JP); Saten Pharmaceutical Co., Ltd., Osaka-fu (JP)" should read --Toshio Hirano, Osaka-fu (JP); Santen Pharmaceutical Co., Ltd., Osaka-fu (JP)--

Signed and Sealed this

Tenth Day of March, 2009

JOHN DOLL  
*Acting Director of the United States Patent and Trademark Office*